United States Patent [19]

Peterson

[11] Patent Number: 5,674,677

[45] Date of Patent: Oct. 7, 1997

[54] IMMUNOASSAY TECHNIQUE USING HISTIDINE TAGS, METALS, AND CHELATING AGENTS

[75] Inventor: Darrell L. Peterson, Chesterfield, Va.

[73] Assignee: The Center for Innovative Technology, Herndon, Va.

[21] Appl. No.: 572,441

[22] Filed: Dec. 14, 1995

Related U.S. Application Data

[63] Continuation-in-part of Ser. No. 360,360, Dec. 21, 1994.

[51] Int. Cl.$^6$ .......................................... C12Q 1/70
[52] U.S. Cl. ...................... 435/5; 435/7.1; 435/7.5; 435/7.6; 435/7.9; 435/7.92; 435/974; 530/323; 530/345; 530/402; 530/403; 530/506
[58] Field of Search .................... 435/5, 7.1, 7.5, 435/7.6, 7.9, 7.92, 974; 530/323, 345, 402, 403, 506

*Primary Examiner*—Christine M. Nucker
*Assistant Examiner*—Jeffrey Stucker
*Attorney, Agent, or Firm*—Whitham, Curtis, Whitham & McGinn

[57] ABSTRACT

Two amino acid sequences are joined together using an electron acceptor moiety and a linking moiety, such as a chelating agent. In particular, an amino acid sequence specific for binding to a material interest is linked to an enzyme which acts on an indicator, such as a colorimetric, phosphometric, fluorometric or chemiluminescent substrate. The linking composition is useful in immunoassays.

9 Claims, 1 Drawing Sheet

IMMUNOASSAY TECHNIQUE USING HISTIDINE TAGS, METALS, AND CHELATING AGENTS

CROSS REFERENCE TO RELATED APPLICATION

This application is a continuation in part of application Ser. No. 08/360,360, filed Dec. 21, 1994.

BACKGROUND OF THE INVENTION

1. Field of the Invention

The present invention generally relates to a technique for joining two amino acid sequences together. The invention has particular utility in linking an amino acid sequence specific for binding to a material of interest to an enzyme which acts on an indicator, such as a colorimetric, phosphometric, fluorometric, or chemiluminescent substrate.

2. Background Description

Enzyme linked immunosorbent assays (ELISAs) are widely used methods for diagnosing an ever increasing number of disease states in man and animals, especially those diseases which are characterized by the presence of specific antibodies in the serum. Some common examples of these types of diseases include hepatitis B virus (HBV), hepatitis C virus (HCV), and human immuno-deficiency viruses (HIV) in humans, and feline immuno-deficiency virus (FIV) and equine infectious anemia virus (EIAV) in animals.

These methods are based on the simple principle of adsorbing an antigen onto a solid phase, and then using the solid phase antigen to capture specific antibodies from a host serum. The captured antibodies are subsequently detected by a variety of methods. The most common method of detection uses an enzyme labeled species specific anti-globulin. A second, but less commonly used, method is to couple an enzyme directly to an antigen which is the same antigen as is bound to the solid phase and then use the enzyme labeled antigen to detect the bound antibody. In these systems, the most widely used enzymatic labels are horse radish peroxidase and alkaline phosphatase.

Enzyme linked anti-globulin is often used for detection since the same labeled reagent can be used in a variety of assays. The use of the enzyme labeled anti-globulin also results in some amplification of the detection signal since more than one anti-globulin can be bound to each captured antibody or immunoglobulin.

The use of enzyme labeled anti-globulin as the detection reagent also introduces some problems. First, the samples to be assayed must be diluted in order to prevent or minimize the non-specific binding of the antibodies or immunoglobulins to the captured antigen. The non-specific binding produces a high background in the assay and a corresponding decrease in the sensitivity of the assay. Second, the antigen which is bound to the solid phase must be pure since there is no specificity in the detection step. Any impurities in the bound antigen would capture unrelated antibodies and would lead to false positive results.

The use of the second method, with an enzyme labeled antigen as the detection reagent is advantageous in that there is no need for dilution of the serum samples, since only antibodies which are specific for the bound antigen will bind to the enzyme labeled antigen. Moreover, although this method lacks the inherent signal amplification which occurs when enzyme labeled anti-globulin is used, the apparent decrease in sensitivity is offset by the fact that no initial dilution of the sample is necessary.

However, the use of enzyme labeled antigen also has disadvantages, in particular, a different labeled antigen is required for each assay, or in other words for each detection assay requires a specific antigen. Furthermore, it is generally necessary to develop a specific labeling methodology for each antigen. Moreover, the direct labeling of the antigen can be difficult, especially if the antigen is either not stable or not reactive under the labeling conditions. It has also been found that the coupling methods which are currently used to link enzymes to antigens have produced an alteration in the antigenicity, which is the subject of the assay.

There is no current method of coupling an enzyme to a protein which overcomes the disadvantages discussed above. In particular, the current methods of antigen labeling can affect the protein characteristics and/or properties. In addition, a different coupling strategy is required for each antigen or protein which is to be labeled. Furthermore, certain proteins cannot be labeled at all or are very difficult to label. Finally, the label is often not stable and can become separated from the protein if the protein-enzyme conjugate is subjected to harsh conditions. Therefore, it is desirable to have a composition for coupling an enzyme to a protein in which the linking composition can be used for all proteins or amino acid sequences and is stable even under harsh conditions. Furthermore, a method for coupling a protein or amino acid sequence to an enzyme which does not alter the characteristics or harm the protein is desirable.

Several techniques have been developed which utilize recombinant methodologies to purify proteins from samples using tagged proteins or the specific interaction between the enzyme-antibody complex and metal ions.

One such technique uses "molecular tagging" procedures to purify proteins in a single step. This tagging method involves the cloning of a short stretch of polyhistidine onto either the amino or carboxy terminus of the protein. The resultant protein, which has a high affinity for nickel ions, is then purified with a nickel affinity column. The affinity of polyhistidine for nickel is great enough that binding occurs even in chaotropic agents such as 6M urea or guanidine hydrochloride.

Another technique is described in U.S. Pat. No. 5,266,686 to Sorenson in which a method for isolating an enzyme-antibody conjugate from a solution which contains both the conjugated and unconjugated enzyme using $Ni^{2+}$ ions bound to a stationary phase. The enzyme-antibody conjugate binds to the $Ni^{2+}$ ions while the free enzyme does not.

SUMMARY OF THE INVENTION

It is therefore an object of the present invention to provide a new technique for joining two amino acid sequences together, and particularly to provide a new technique for joining an amino acid sequence which specifically binds to a material of interest together with an enzyme which can cleave a detecting reagent, such as a colorimetric reagent, chemiluminescent reagent, fluorometric reagent, phosphometric reagent, or the like.

It is another object of this invention to provide novel compositions useful in immunoassays where the compositions include an amino acid sequence which binds to a material of interest joined to an enzyme that can act on a detecting reagent, wherein the two components of the composition are joined together by an electron acceptor moiety, such as a metal ion or the like, that interacts with one amino acid sequence, and a linking moiety, such as a chelating agent or the like, which interacts with the enzyme.

It is also an object of this invention to provide a composition which can detect antibodies which are present in low amounts.

It is another object of this invention to provide a composition for linking an enzyme to a protein which can be used on all proteins and does not modify the protein.

According to the invention, two amino acid sequences are connected together by an electron acceptor moiety associated with one of the amino acid sequences and a linking moiety associated with the other amino acid sequence. Particularly good results are obtained when the electron acceptor is a metal ion and the linking moiety is a chelating agent. In a specific application of this invention related to immunoassays, enzymes and proteins are joined together. Experiments have demonstrated that the coupling of enzymes to recombinant proteins using molecular tagging methodology can be used in direct sandwich immunoassays to detect antibodies. It has been found that this method of coupling increases the detection of antibodies in serum. Furthermore, the composition can be used to label all proteins. In addition, although the labeling can occur under mild conditions, the enzyme amino acid or protein conjugate can also withstand harsh conditions and therefore can be used in a variety of applications which require an enzyme labeled protein.

BRIEF DESCRIPTION OF THE DRAWINGS

The foregoing and other objects, aspects and advantages will be better understood from the following detailed description of a preferred embodiment of the invention with reference to the drawings, in which:

FIG. 1A is an illustration of the stained gel obtained from blotting purified proteins and whole cell extracts which contain tagged protein; and FIG. 1B shows the binding of α-N,N bis[carboxymethyl] lysine (CM-lys) modified peroxidase to the gel.

DETAILED DESCRIPTION OF A PREFERRED EMBODIMENT OF THE INVENTION

Figure 1A:
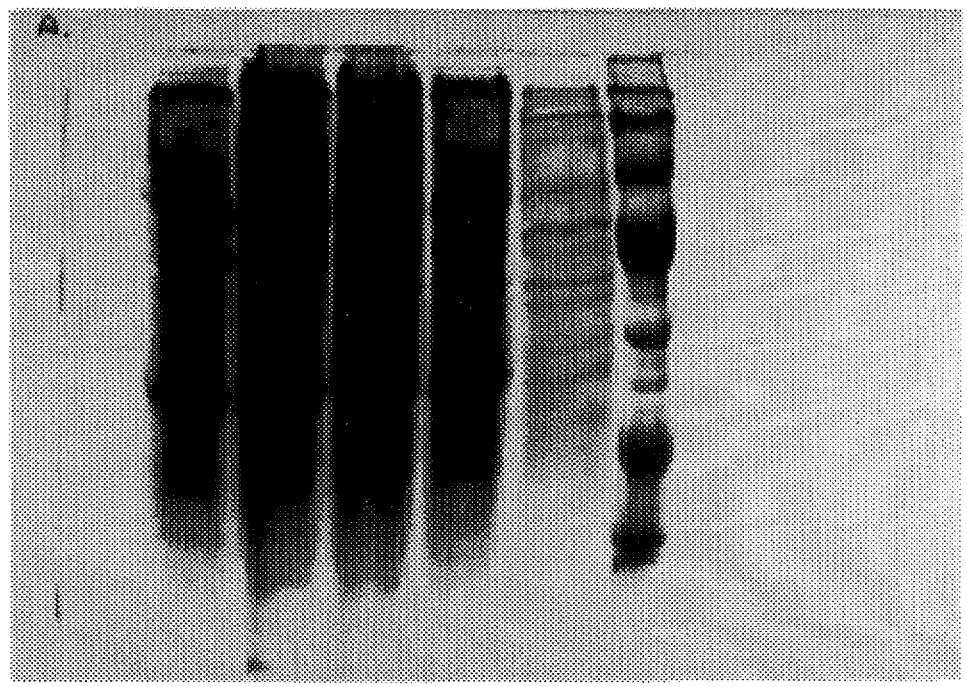
FIGS. 1A–1B illustrate a gel obtained from blotting tagged proteins.

It has been discovered that an enzyme can be coupled to an amino acid sequence by an organic chelator and metal ion and that this method of coupling can be used with numerous amino acid sequences including a variety of proteins and in particular, antigens. In addition, it has been found that the novel composition for linking the enzyme to the antigen does not affect the properties or characteristics of the antigen.

In a specific application, the composition of the present invention utilizes an organic chelator and a metal ion to label a protein with an enzyme. An organic chelator, such as nitrilotriacetic acid (NTA), iminodiacetic acid (IDA), bicinchoninic acid (BCA) or N,N,N'-tris(carboxymethyl) ethylenediamine (TED), is coupled to an enzyme. The organic chelator is then charged with a metal ion. This complex can then be mixed with any protein which contains a histidine "tag" so that the enzyme is coupled to the histidine tagged protein.

As a specific example, an organic chelator, in this case a compound with an NTA functional group, CM-lys, is synthesized using published methods from epsilon amino blocked lysine reacted with bromoacetate, as is shown below.

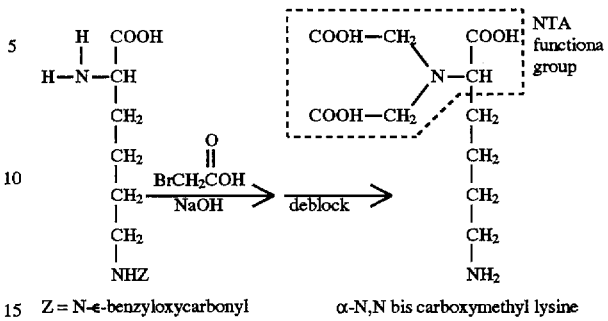

Z = N-ε-benzyloxycarbonyl    α-N,N bis carboxymethyl lysine

In the practice of the invention, any compound with the appropriate functional group can be used including tyrosine or cysteine with an NTA functional group and all of the chelating ligands discussed supra.

The CM-Lys is then bound to an enzyme, such as horse radish peroxidase or to a protein. However, it is possible to use other enzymes such as alkaline phosphatase, beta galactosidase or luciferase. Other proteins such as phycobiliproteins could also be used.

If horse radish peroxidase is used the enzyme can be bound through the epsilon amino group using reductive alkylation with periodate activated peroxidase, making the following bond.

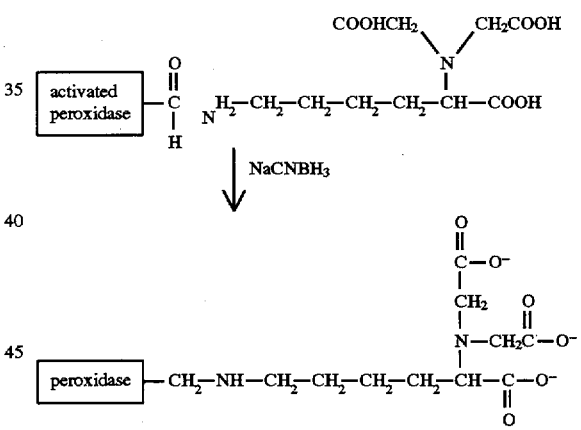

However, it is anticipated that other methods of coupling and other enzymes and organic chelators can be used. The key feature in the first step is to join an amino acid sequence, such as an enzyme or the like, together with a linking moiety.

Continuing with the exemplary case where the linking moiety is an organic chelator such as CM-Lys, the next step is to add a suitable electron acceptor that can be bound to the linking moiety. A particularly preferred electron acceptor is $Ni^{2+}$. However, it is expected that other metal ions such as $Cu^{2+}$ or $Zn^{2+}$ can also be used.

In the example, to charge the organic chelator, nickel chloride is added and then dialyzed to form the Ni-NTA-peroxidase, as is shown below.

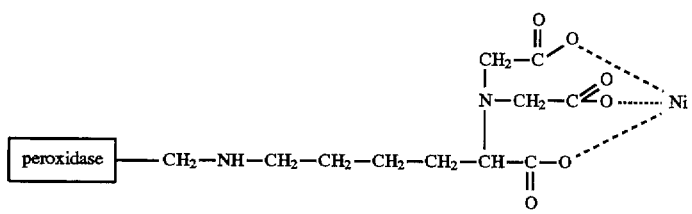

This complex of an organic chelator, NTA, a metal ion, Ni and an enzyme, horse radish peroxidase is then mixed with any protein or amino acid sequence which contains a histidine tag. A histidine tag is a sequence of three or more adjacent histidines which are generally on the carboxy or amino terminus end of the protein or amino acid sequence. However, it is expected that any accessible sequence of histidines could be used within the practice of the invention. Histidine tags can be added to the protein or amino acid sequence during the cloning of the protein or amino acid sequence. The polyhistidines on the protein or amino acid sequence bind very tightly to the Ni-NTA-peroxidase complex producing a composition which can be used for a variety of systems which require the binding of a protein to an enzyme or to another protein.

An important feature of the above example is that a portion of a second amino acid sequence is joined to the first amino acid sequence by interacting with the electron acceptor moiety (metal ion, etc.) which is joined to the linking moiety (NTA functional group, etc.), which itself is joined to the first amino acid sequence (enzyme, protein, etc.).

The following examples demonstrate the beneficial effects of using an organic chelator-metal ion complex as a linker between an enzyme and a protein and its use in diagnostic assays for antibodies against immunoassays of hepatitis B, including HBcAG and HBsAG, hepatitis C, and retro viruses, including HIV, EIAV, and FIV and other related conditions which can be diagnosed by the presence of antibodies in humans and animals.

EXAMPLE 1

This Example details the experimental results which demonstrate the ability of the linker complex to specifically bind to the histidine tagged proteins.

Materials and Methods: Nitrilotriacetic acid, horse radish peroxidase, chloronaphthol, hydrogen peroxide, sodium cyanoborohydride, and periodic acid, were obtained from Sigma (St. Louis, Mo.). Microtitre plates, manufactured by Coming, were obtained from Fisher (Columbia, Md.). TM Blue was obtained from TSI (Milford, Mass.).

Preparation of α-N,N bis[carboxymethyl]lysine (CM-lys). ε-N-benzyloxycarbonyl lysine (ε-Z-lys) was obtained from Advance Chemtech (Louisville, Ky.); bromoacetic acid was obtained from Sigma (St. Louis, Mo.). Carboxymethylation of ε-Z-lys was performed in 2M sodium hydroxide by the slow addition of a 2.5 molar excess of bromoacetic acid which had been dissolved in 2M sodium hydroxide. The reaction was allowed to proceed on ice for 4 hours, and then at room temperature for 24 hours, and finally at 50° C. for 2 hours. Following the reaction, the modified Z-lys was purified by recrystallization following the addition of HCl to pH 2, and the Z group was removed by catalytic hydrogenation. The extent of reaction was determined by amino acid analysis by following the disappearance of the starting amino acid.

Coupling of α-N,N[carboxymethyl]lysine to horse radish peroxidase. Horse radish peroxidase (100 mg) was dissolved in 25 ml of 50 mM phosphate buffer, pH 6.8. Sodium periodate was added to a final concentration of 0.02M and allowed to react at room temperature for 20 min., and then the enzyme solution was dialyzed overnight against 1 mM acetate buffer, pH 4.

CM-lys was then coupled to the enzyme by reductive alkylation as follows. CM-lys was added to the activated horse radish peroxidase to a final concentration of 20 mM, in borate buffer, 50 mM pH 8.8, and 10 mM sodium cyanoborohydride. The reaction was allowed to proceed for 4 hours at room temperature. Nickel sulfate was added to a final concentration of 50 mM and excess reagents were removed by extensive dialysis against water. The modified peroxidase was stable for months at 4 ° C., but was routinely stored frozen in small aliquots. The peroxidase activity of the enzyme was unaffected by this procedure, as determined by its specific activity when TM blue was used as substrate.

Measurement of Nickel Content. The concentration of nickel in the CM-Lys modified horse radish peroxidase was determined by atomic absorption at 232 nm with an Instrumentation Laboratory, Inc., model Video 22 atomic absorption spectrometer. A series of standards ranging in concentration from 0 to 5.0 µg/ml was used to establish the relationship between absorbance and nickel concentration.

Recombinant Proteins. Table 1 summarizes the recombinant proteins used in these studies.

TABLE 1

| PROTEIN | LENGTH amino acids | HISTIDINE TAG POSITION | PHYSICAL PROPERTIES |
|---|---|---|---|
| HBV core | 181 | untagged | Product of the translation of nucleotides 1903-2450 of the ayw subtype of HBV; soluble, macromolecular particle; 26 nm in diameter; probably 180 subunits |
| HBV truncated core | 157 | carboxy terminal | Product of the translation of nucleotides 1903-2349 of the ayw subtype of HBV, plus codons for 6 terminal histidine residues; soluble, macromolecular particle; indistinguishable from the native core protein by electron microscopy, although the carboxy deleted and the histidine has been added. |
| HCV core | 180 | carboxy terminal | Product of the translation of a chemically synthesized gene coding for a protein of the same sequence as nucleotides 1-552 of the HCV; poorly soluble in the absence of chaotropic agents, soluble in 6 M urea; monomeric under these conditions. |
| HCV NS#3 (helicase) | 450 | amino terminal | Product of the translation of nucleotides 3616-4972 of the HCV, plus codons for the amino terminal extension of 6 histidines, and a short leader sequence coding amino acids; soluble; monomeric; enzymatically active. |

TABLE 1-continued

| PRO-TEIN | LENGTH amino acids | HISTI-DINE TAG POSI-TION | PHYSICAL PROPERTIES |
|---|---|---|---|
| CAEV core | | carboxy terminal | Product of the translation of nucleotides 512-1258 of the CAEV; soluble; monomeric. |
| FIV core | | carboxy terminal | Product of the translation of nucleotides 1033-1713 of the petaluma strain of FIV; soluble; monomeric. |
| HBV pre-S | 153 | untagged | Product of the translation of nucleotides 2850-155 of the ayw subtype of HBV; soluble; monomeric. |
| HBV pre-S | 159 | carboxy terminal | Product of the translation of the nucleotides 2850-155, as above, except for the addition of codons for 6 terminal histidine residues; soluble; monomeric. |

These proteins were chosen because of their potential usefulness in diagnostic assays, and also because they vary greatly in their physical properties. The proteins include small soluble proteins, large soluble macromolecular proteins and insoluble proteins.

Labeling of Recombinant Proteins with Peroxidase: In general, equimolar amounts of the recombinant protein and CM-lys modified peroxidase were mixed at pH 7.5, and then diluted to a final peroxidase concentration of 1 µg/ml in 10% bovine serum albumin (BSA). The coupling step is essentially instantaneous. In order to obtain the maximum sensitivity in an assay, the optimum ratio of the two proteins is determined empirically by mixing the proteins at several different ratios and comparing the results to obtain the combination which gives the highest signal and lowest background.

Immunoassays: ELISAs were performed in standard 96 well microtitre plates (Corning). The plates were coated with antigen (recombinant protein) at a concentration of 5–20 µg/ml in bicarbonate buffer, pH 9.5 for 18 hours at room temperature, and then washed with phosphate buffered saline (PBS) containing 0.1% tween 20. Plates were air dried and stored a −20 ° C. until used. The ELISAs were performed by adding 50–200 µl of serum (undiluted, or diluted in negative serum of the same species), and incubating for 30 minutes at room temperature. The plates were then washed three times with PBS/tween. Peroxidase-conjugated antigen was added (50 µl per well) and incubated for 15 minutes at room temperature. The plate was then washed with PBS/tween, and 50 µl of substrate was added (TM blue). Color was allowed to develop (generally 10 minutes), and then the reaction was stopped by the addition of 100 µl of 1N sulfuric acid. The plates were read in a Dynatech microtitre plate reader at 450 nm.

Blotting with CM-Lys modified Peroxidase: SDS polyacrylamide gel electrophoresis was performed according to the method of O'Farrell, P. H., J. Biol. Chem., 250, 4007–4021, and the proteins electrophoretically transferred to nitrocellulose membranes as previously described in Burnette, W. N., Anal. Biochem., 112, 195–203. The membranes were blocked by incubating with a solution ion of 4% BSA in PBS for 30 minutes, and then CM-Lys-modified peroxidase was added to a final concentration of 1 µg/ml. The membrane was incubated for 4 hours at room temperature with shaking, and then washed extensively with PBS tween. Substrate (chloronapthol/peroxide) was added and the color allowed to develop for 10 minutes, and then the reaction was stopped by washing.

RESULTS: Preparation of the CM-lys modified Peroxidase: The carboxymethylation reaction proceeded to completion to yield a-N, N[carboxymethyl]lysine as judged by the complete disappearance of lysine in the final product upon amino acid analysis. The compound coeluted with glycine in the system which was used, and also gave a very low color value. Thus the extent of incorporation of this compound into the peroxidase could not be determined directly by amino acid analysis. However, the number of groups was estimated by determining the number of nickel (Ni) ions bound per mole of peroxidase by atomic absorption spectroscopy. Based on the value of 40,000 for the molecular weight of peroxidase, 10–12 nickel ions were bound per molecule of peroxidase.

Figure 1B:
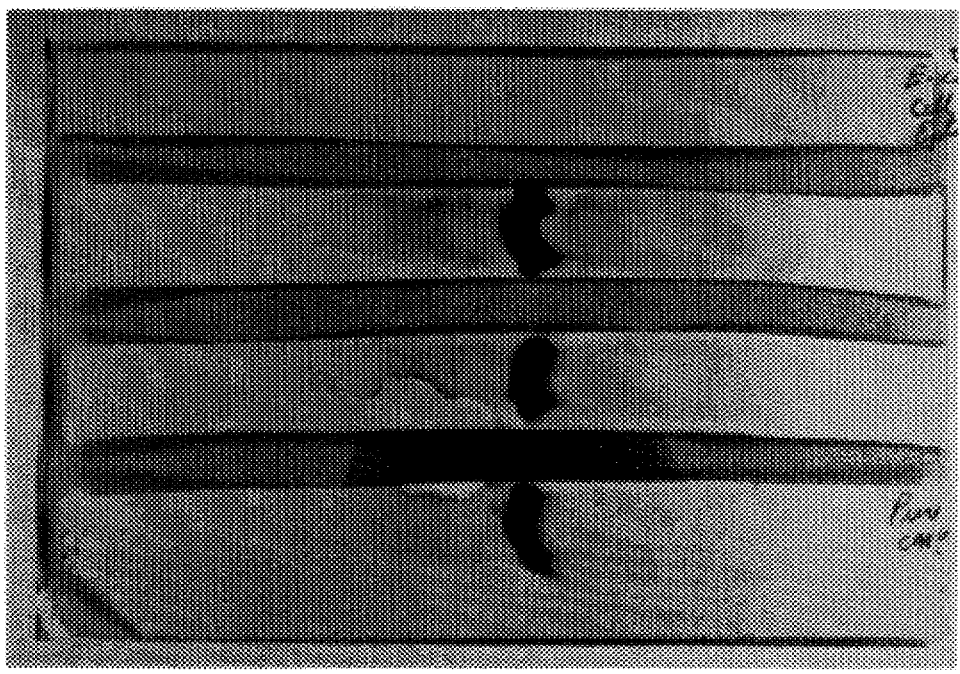

Binding of CM-lys modified Peroxidase to Histidine tagged proteins. In order to determine if the modified peroxidase would bind to histidine tagged proteins, the compound was first used to bind directly to the protein which had been blotted onto nitrocellulose. FIGS. 1A and 1B show the results of the blotting of the purified proteins (CAEV core) and the whole cell (*E. coli*) extracts containing the tagged protein. FIG. 1A shows the stained gel, while FIG. 1B shows the binding of the CM-Lys peroxidase to the gel. It is clear that the peroxidase binds the cloned viral protein and not to the normal cellular proteins. The same results were obtained with the other proteins. (data not shown)

Table 2 shows that the CM-Lys-peroxidase binds to the purified histidine tagged proteins which have been coated onto microtitre wells.

TABLE 2

| | $A_{450}$ | | | |
|---|---|---|---|---|
| micrograms | UNMODIFIED PEROXIDASE | | CM-Lys PEROXIDASE | |
| peroxidase added | non-tagged protein | histidine tagged protein | non-tagged protein | histidine tagged protein |
| 0 µg/ml | 0.00 | 0.01 | 0.02 | 0.05 |
| 2.0 µg/ml | 0.01 | 0.05 | 0.00 | 1.60 |
| 1.0 µg/ml | 0.01 | 0.03 | 0.02 | 0.86 |
| 0.5 µg/ml | 0.02 | 0.03 | 0.01 | 0.53 |

It can also been seen from Table 2 that the proteins which lack the histidine extension do not bind to the CM-Lys peroxidase, and furthermore, that both the untagged and tagged protein do not bind to the unmodified peroxidase.

The experimental data clearly shows that the enzyme labeling of the peroxidase is adequate, and that the peroxidase is readily and specifically bound to histidine tagged proteins.

EXAMPLE 2

This example details the experimental results which demonstrate the ability of the composition of the organic chelator, metal ion, enzyme and protein to detect antibodies which are produced in response to variety of viruses. Examples of different ELISAs using the CM-Lysperoxidase are provided which illustrate the usefulness of the composition. In addition, experimental data has been provided to show the preferred methods for circumventing some common issues regarding the binding of unbound peroxidase directly to wells coated with a histidine tagged protein which can produce false positive results.

Assay format 1. It is preferred that the antigen is available as both a non-tagged and a histidine tagged protein. This enables the non-tagged protein to be used as the capture antigen so that any free peroxidase is prevented from binding to the antigen which is bound to the solid phase.

The following is an illustration of this assay format using the hepatitis B virus (HBV) pre-S protein. The cloning and isolation of this protein has been previously described in Delos, S., Villar, M. T., Hu, P., and Peterson, D. L. Biochem. J. (1991) 276, 411-416, which is herein incorporated by reference. The protein is expressed as a soluble protein and approximately 50 mg of protein are obtained per liter of culture using standard protein isolation methods. This protein was used to coat microtitre plates at a concentration of 10 µg/ml. In this experiment, the plates were coated in 20 mM citric acid, pH 3. The pre-S gene was subsequently modified to include codons for a carboxy terminal extension of six histidine residues, and then cloned into the same expression vector (pET 3d). The incorporation of the histidine tag did not affect the expression level or physical properties of the protein. The soluble, monomeric, histidine tagged protein was labeled with peroxidase by mixing equimolar amounts in Tris/HCl buffer, pH 7.5. The labeled protein was diluted in 10% BSA for use in assays.

Table 3 shows the results of assaying rabbit serum for anti-HBsAg pre-S antibodies raised against the non-tagged pre-S protein using the CM-Lys modified peroxidase.

TABLE 3

| SERUM DILUTION | ABSORBANCE AT 450 NM (pure pre-S) | ABSORBANCE AT 450 NM (E. coli extract) |
|---|---|---|
| negative control | 0.02 | 0.05 |
| undiluted positive | >2.0 | >2.0 |
| 1:10 | >2.0 | >2.0 |
| 1:20 | >2.0 | >2.0 |
| 1:40 | 1.3 | 1.42 |
| 1:80 | 0.65 | ND |
| 1:160 | 0.30 | ND |
| 1:320 | 0.13 | ND |

The negative serum gave absorbance values of less than 0.05, while the positive serum gave values of greater than 2. The positive serum remained clearly positive even at a dilution of 1:160 in normal rabbit serum. It can also be seen from Table 3 that the protein does not need to be purified in order to label it, since the labeling reagent, CM-lys-peroxidase, is specific for the histidine tagged protein. It is shown that the use of an E. coli extract containing the histidine-tagged protein mixed with the CM-lys modified peroxidase produced the same assay results as with the purified proteins. It is also shown that the protein which is used on the solid phase to capture the antibodies does not need to be pure, since only the specific antibodies are detected by the peroxidase labeled antigen. However, it should be noted that if the bound protein is contaminated, the sensitivity of the might be lowered, since the contaminant proteins would compete for binding sites of the solid phase and therefore, lower binding of the desired protein would be expected.

' Assay format 2. It is also possible to use the protein with the histidine tag for both the capture and the coating protein, particularly in situations where the protein lacking the histidine tag is not available. However, it has been found that if the untagged protein is not available, a modification in the method, described above, may be required.

An illustration of assay format 2 is provided below using an assay for antibodies against the HCV NS3 protein, CAEV and FIV core proteins. In these experiments, microtitre plates were coated with the purified histidine tagged proteins, and the same proteins were also coupled to peroxidase by mixing equimolar amounts followed by dilution in 10% BSA in Tris/HCl, pH 7.5. To prevent any un-bound peroxidase, or peroxidase with unsatisfied ligands, from binding directly to the plate, the histidine tagged protein on the plates was blocked by incubation with 300 mM nitrilotriacetate/Ni complex (prepared by mixing equimolar amounts of nitrilotriacetate and nickel sulfate), in Tris/HCl, pH 8.0 for 2 hours, followed by washing with PBS tween. In addition, this same complex (10 mM, final concentration) was added to the antigen-peroxidase conjugate solution.

Table 4 shows the results of ELISAs using CM-Lysperoxidase with solid phase histidine tagged proteins and using positive and negative sera. The values reported are the average of the absorbance values at 450 nm of duplicate determinations on two or more different undiluted serum samples for each.

TABLE 4

| | SOLID PHASE PROTEIN USED | | | | |
|---|---|---|---|---|---|
| | HCV NS3 | CAEV core | HCV core | FIV core | BIV core |
| negative sera | 0.012 | 0.04 | 0.02 | 0.01 | 0.02 |
| positive sera | 0.03 | 0.02 | 0.04 | 0.02 | |
| | 1.65 | 1.86 | >2.0 | 0.77 | 1.12 |
| | >2.0 | 1.7 | 1.4 | 1.14 | 0.83 |

As noted above, the results provided in Table 4 show that negative sera gave very low background, while positive sera gave high absorbance. The same method was found to give good results with the HIV core protein. (data not shown) It is also shown that the blocking step with the nickel-NTA complex was effective, since after the blocking step the CM-lys-peroxidase does not bind directly to the ELISA wells.

It is also known that many recombinant proteins are poorly soluble in the absence of detergents or chaotropic agents such as urea and guanidine. Therefore, as discussed above, it is necessary to provide a composition to link the enzyme to the protein which can withstand harsh conditions. An example of a poorly soluble protein and the ability of a metal ion-organic chelator link to withstand harsh conditions is provided below.

The hepatitis C virus core protein is an example a protein which is not soluble at high concentrations in Tris/HCl, pH 7.5. However, it is readily soluble in 5 M guanidine HCl, pH 7.5. The protein, which as been solubilized in guanidine, remains in solution when diluted to the low concentration used for coating microtitre plates (10 µg/ml), and so is readily used as the capture antigen in ELISA. Moreover, the antigen is readily coupled to the derivatized peroxidase by mixing the HCV core protein, dissolved in 5M guanidine, with equimolar amounts of peroxidase dissolved in PBS, followed by immediate dilution to the usual peroxidase concentration (1 µg/ml). Since the binding of the peroxidase to the histidine-tagged protein proceeds quickly and the mixture is diluted immediately, the peroxidase does not lose its activity.

The results of the assaying of human sera for anti HCV core antibodies using this method are shown above in Table 4. The NTA/Ni blocking step, described above, was used in these experiments, since histidine tagged protein was also used as the capture antigen.

A further issue which must be considered is the accessibility of the histidine tag, particularly due to the structure of the protein, such that the protein will not bind to the CM-lys derivatized peroxidase. One example of this is the hepatitis B core protein (HBcAg), having a carboxy terminal histidine tag. In this case, the histidines are hidden within the particle interior. However, 3M thiocyanate was found to expose the histidine tag, while not destroying the HBcAg epitopes.

Table 5 shows the results of using a CM-lys-peroxidase conjugated to HBcAg to assay human sera for antibodies against HBcAg. Table 5

| SAMPLE NO. | $A_{450}$ | RESULTS OF PREVIOUS ASSAY | SAMPLE NO. | $A_{450}$ | RESULTS OF PREVIOUS ASSAY |
|---|---|---|---|---|---|
| 1 | 0.00 | 1.718 (−) | 13 | 0.41 | 0.152 (+) |
| 2 | 0.09 | 1.650 (−) | 14 | 0.79 | 0.107 (+) |
| 3 | 0.13 | 1.784 (−) | 15 | 0.69 | 0.152 (+) |
| 4 | 0.10 | 1.712 (−) | 16 | 0.52 | 0.149 (+) |
| 5 | 1.31 | 1.442 (−) | 17 | 0.80 | 0.142 (+) |
| 6 | >2.0 | 0.267 (+) | 18 | 0.63 | 0.107 (+) |
| 7 | 1.70 | 0.365 (+) | 19 | >2.0 | 0.155 (+) |
| 8 | 0.62 | 0.196 (+) | 20 | 1.56 | 0.132 (+) |
| 9 | 0.88 | 0.221 (+) | 21 | 0.54 | 0.142 (+) |
| 10 | 0.78 | 0.185 (+) | 22 | 0.76 | 0.155 (+) |
| 11 | 0.45 | 0.214 (+) | 23 | 0.96 | 0.161 (+) |
| 12 | 0.63 | 0.167 (+) | 24 | 0.80 | 0.137 (+) |

In this experiment, the capture antigen was the untagged full length core protein. The peroxidase conjugate was prepared by adding equimolar amounts of histidine tagged HBcAg, dissolved in 3M potassium thiocyanate and CM-lys-peroxidase, dissolved in Tris/HCl, pH 7.5, followed immediately by dilution in 10% BSA in PBS.

Table 5 presents a series of sera which constitute a seroconversion panel obtained from Serologics, Inc. This panel includes 25 samples of sera taken from a single infected individual at approximately weekly intervals during the course of a natural infection with HBV. The values presented are the absorbencies observed. It is clear from this data that the negative values are very low and that the positive values can be easily distinguished. The table also provides the results of commercial competitive ELISAs for antibodies against HBcAg. The positive and negative assignments are the interpretations of the values according to the manufacturer of the assay. It should be noted, as can be seen from the data presented in Table 5, assays using the metal ion-organic chelate complex, as described herein, were able to detect the seroconversion one week earlier, at sample 5 rather than sample 6, than the commercial assay.

The experimental data, set forth above, clearly demonstrates that CM-lys modified peroxidase is an effective general labeling reagent for use with histidine tagged proteins. The composition of an organic chelator-metal ion complex to bind a protein to an enzyme can be used in ELISAs to detect antibodies in serum.

It has been shown that the method and composition can be used with both soluble and insoluble proteins as well as with pure or impure proteins. Since these proteins are exemplary of broad and diverse classes of proteins, it is expected that this composition and method will be useful for binding most amino acid sequences to a labeling compound.

Furthermore, the availability of numerous bifunctional crosslinking reagents enables that the organic chelator-metal ion complex can be coupled to any protein or macromolecule, and subsequently used as a reporter group to attach to histidine tagged proteins.

The method can also be used in other applications. For example, enzyme labeled proteins can be used to study the interaction between a protein and cell receptors. Since the labeling method of labeling discussed supra, enables the enzyme labeling to be specifically targeted to either the carboxy or amino terminus of a protein, it is able to provide a construct which is less likely to interfere with the putative binding site of the protein.

While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. An assay method, comprising the steps of:

combining a labeled amino acid sequence specific for an amino acid sequence of interest in a sample, said labeled amino acid sequence comprising
  i) a histidine tag,
  ii) an enzyme covalently bonded to a chelating agent, and
  iii) a metal electron acceptor, wherein said enzyme is linked to said histidine tag by said metal electron acceptor which bonds with both said chelating agent and said histidine tag;

allowing said labeled amino acid sequence to bind to said amino acid sequence of interest in said sample; and measuring the amount of labeled amino acid sequence bound to said amino acid sequence of interest.

2. The method of claim 1 wherein said step of measuring includes the steps of:

adding an indicator substrate clearable by said enzyme covalently bound to said chelating agent of said labeled amino acid sequence; and measuring a cleaved reaction product derived from said indicator substrate from said enzyme cleaving said indicator substrate.

3. The method of claim 1 further comprising the step of binding said labeled amino acid sequence to a solid phase.

4. The method of claim 1 further comprising the step of binding said amino acid sequence of interest to a solid phase.

5. The method of claim 1 wherein said step of combining is performed in the presence of a non-labeled amino acid sequence specific for said amino acid sequence of interest, said non-labeled amino acid sequence being identical to said labeled amino acid sequence in all respects except that it lacks said histidine tag, said enzyme covalently bonded to a chelating agent, and said metal electron acceptor.

6. A method as in claim 1 wherein said amino acid sequence of interest is elicited by Bovine Immunodeficiency Virus.

7. A method as in claim 1 wherein said amino acid sequence of interest is elicited by Feline Immunodeficiency Virus.

8. A method as in claim 1 wherein said amino acid sequence of interest is elicited by Caprine Arthritis and Encephalitis Virus.

9. A method as in claim 1 wherein said amino acid sequence of interest is elicited by Hepatitis C Virus.

* * * * *